(12) United States Patent
Kim et al.

(10) Patent No.: US 8,193,340 B2
(45) Date of Patent: Jun. 5, 2012

(54) PREPARATION METHOD OF POROUS HYALURONIC ACID SPONGE FOR CELL DELIVERY SYSTEM

(75) Inventors: Dae-Duk Kim, Kwanak-gu (KR); Jeong-Yeon Kang, Seoncho-gu (KR); Chung-Wook Chung, Yuseong-gu (KR); In-Soo Yoon, Gwanak-gu (KR); Sun-Young Kim, Gwanak-gu (KR); Byung-Soon Park, Gangnam-gu (KR); Jong-Hyuk Sung, Gwanak-gu (KR)

(73) Assignees: Seoul National University Industry Foundation, Seoul (KR); Prostemics Co., Ltd., Seoul (KR)

( * ) Notice: Subject to any disclaimer, the term of this patent is extended or adjusted under 35 U.S.C. 154(b) by 829 days.

(21) Appl. No.: 12/299,496

(22) PCT Filed: May 2, 2007

(86) PCT No.: PCT/KR2007/002162
§ 371 (c)(1),
(2), (4) Date: Nov. 4, 2008

(87) PCT Pub. No.: WO2007/129828
PCT Pub. Date: Nov. 15, 2007

(65) Prior Publication Data
US 2011/0268706 A1 Nov. 3, 2011

(30) Foreign Application Priority Data

May 4, 2006 (KR) .................. 10-2006-0040652
May 2, 2007 (KR) .................. 10-2007-0042611

(51) Int. Cl.
*C08B 37/00* (2006.01)
*C07H 5/04* (2006.01)
*C07H 5/06* (2006.01)
*A61K 9/14* (2006.01)
*A61K 31/715* (2006.01)
*A01N 43/04* (2006.01)

(52) U.S. Cl. .................. 536/55.3; 424/488; 514/54
(58) Field of Classification Search .................. None
See application file for complete search history.

(56) References Cited

FOREIGN PATENT DOCUMENTS

| JP | 2000230003 A | 8/2000 |
|---|---|---|
| JP | 2003055402 A | 2/2003 |
| KR | 1020000025222 A | 5/2000 |
| KR | 1020050042517 A | 5/2005 |

OTHER PUBLICATIONS

Lee et al. KR2000-0025222, May 6, 2000, machine translation.*
International Preliminary Report on Patentability for PCT/KR2007/002162 mailed Aug. 25, 2008 by IPEA/KR.
International Search Report for PCT/KR2007/002162 mailed Aug. 13, 2007 by ISA/KR.

* cited by examiner

*Primary Examiner* — Layla Bland
(74) *Attorney, Agent, or Firm* — Sherr & Vaughn, PLLC

(57) ABSTRACT

Provided is a preparation method of a porous hyaluronic acid sponge comprising the steps of: dissolving hyaluronic acid in an aqueous sodium hydroxide solution; adding an epoxy-based crosslinking agent to the resultant aqueous sodium hydroxide solution in which hyaluronic acid is dissolved and homogenizing the hyaluronic acid solution; hydrogelating the homogenized hyaluronic acid solution; washing the hydrogelated hyaluronic acid hydrogel with ultrapure water; swelling the washed hyaluronic acid hydrogel to attain porosity; and freeze-drying the hyaluronic acid hydrogel to obtain a porous hyaluronic acid sponge.

7 Claims, 6 Drawing Sheets

[Fig. 1]
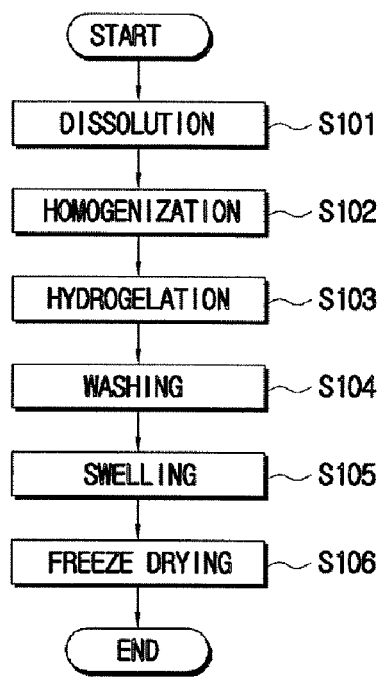
[Fig. 2]
[Fig. 3]
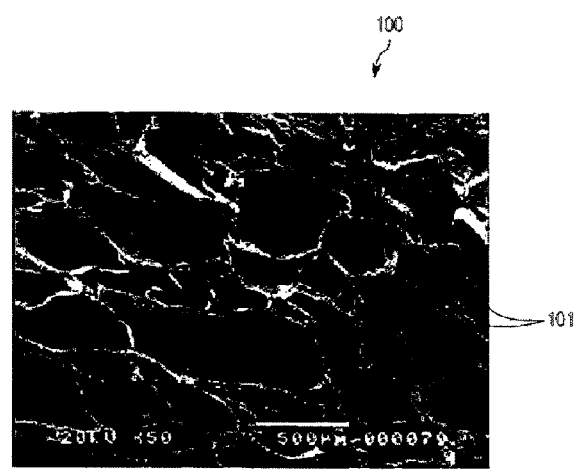

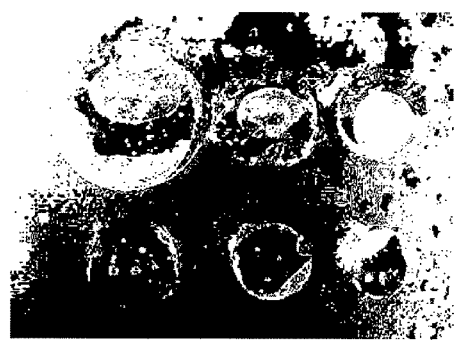
[Fig. 4]
[Fig. 5]
[Fig. 6]
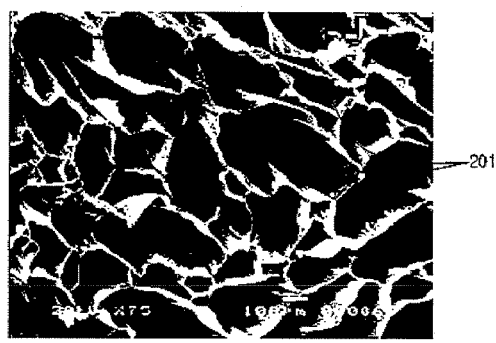
[Fig. 7]
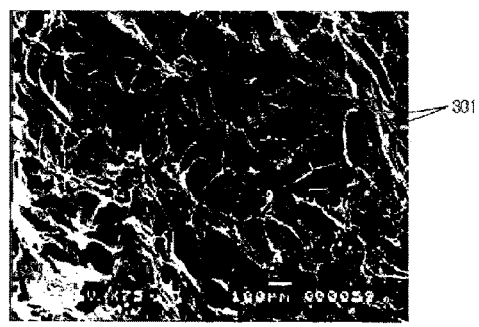

[Fig. 8]
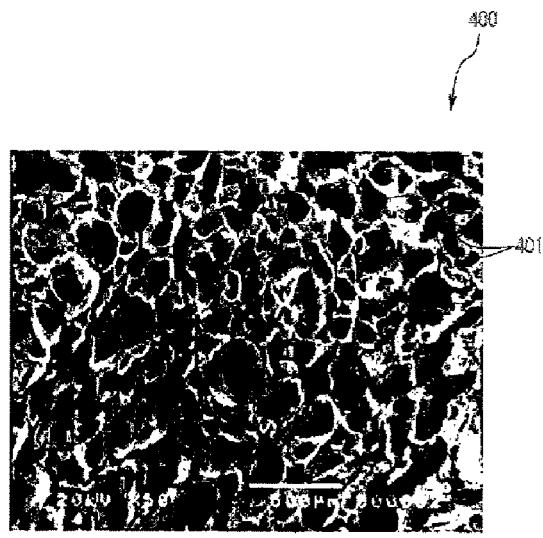
[Fig. 9]
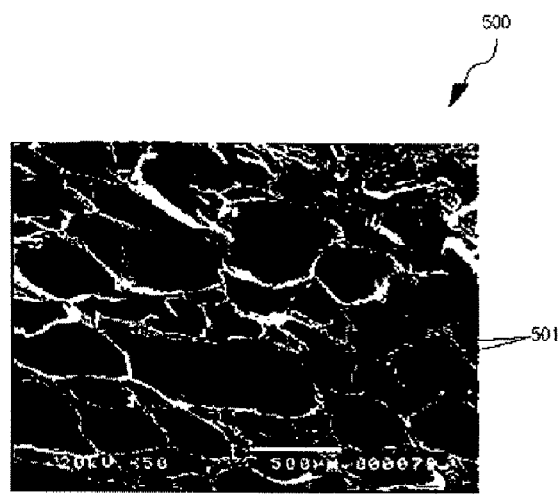
[Fig. 10]
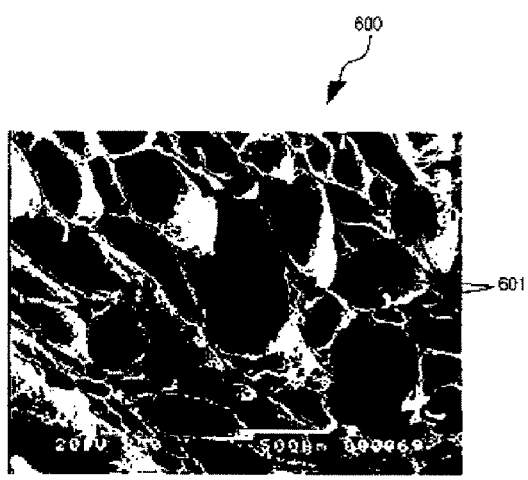

[Fig. 11]
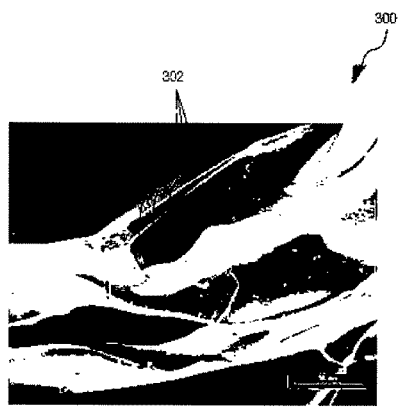
[Fig. 12]
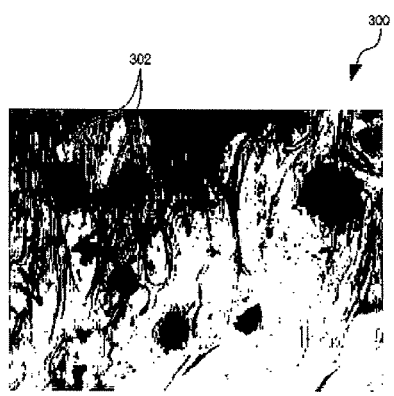
[Fig. 13]
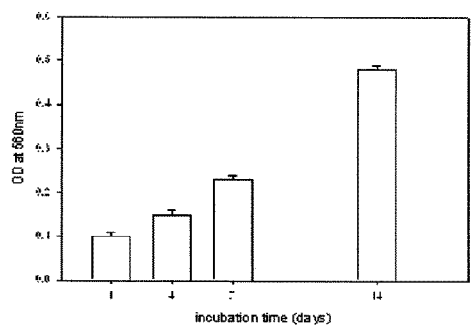
[Fig. 14]
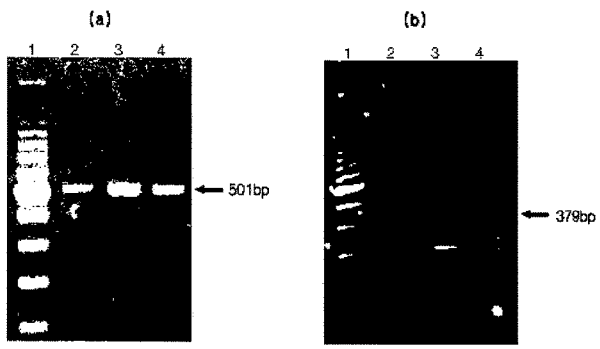

[Fig. 15]
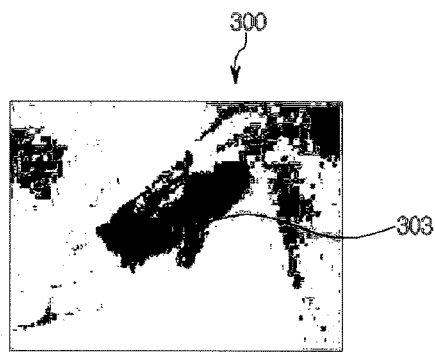
[Fig. 16]
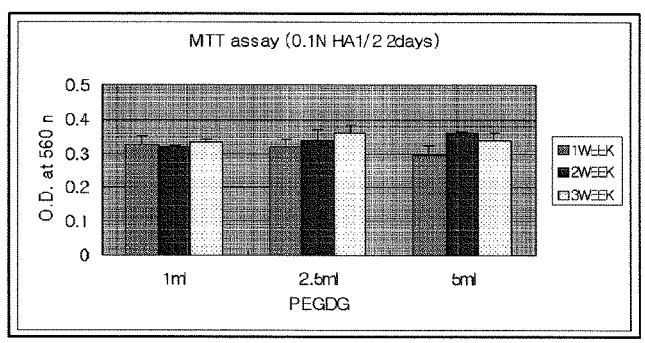
[Fig. 17]
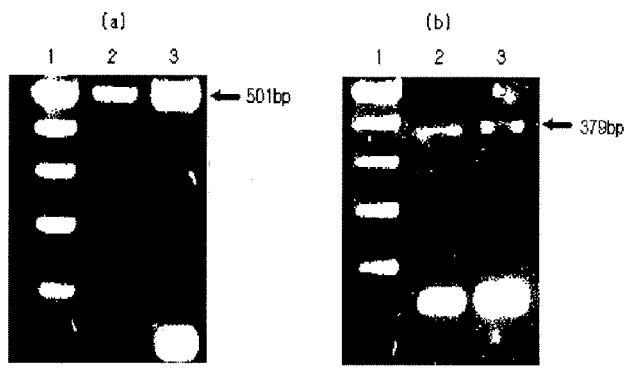
[Fig. 18]
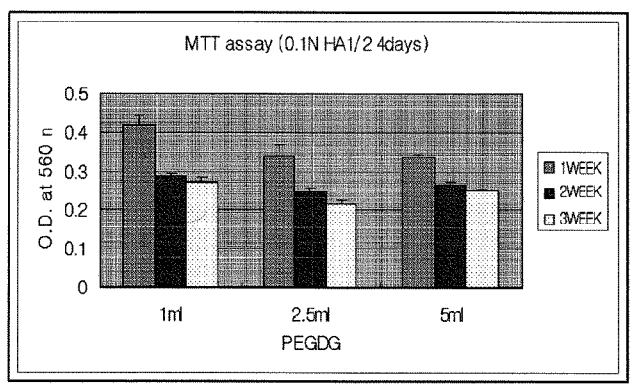

[Fig. 19]
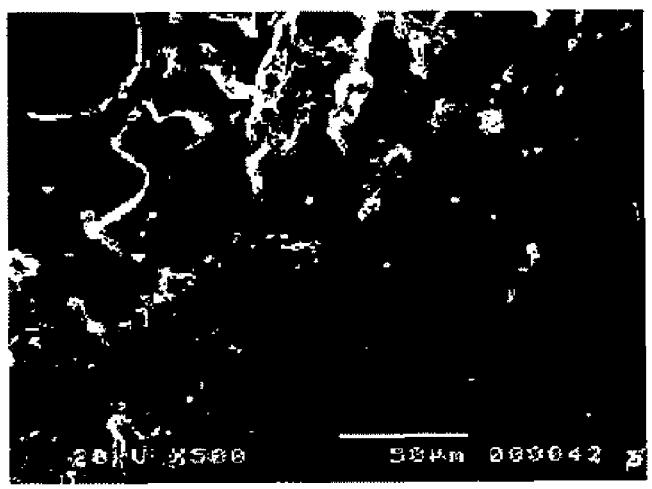
[Fig. 20]
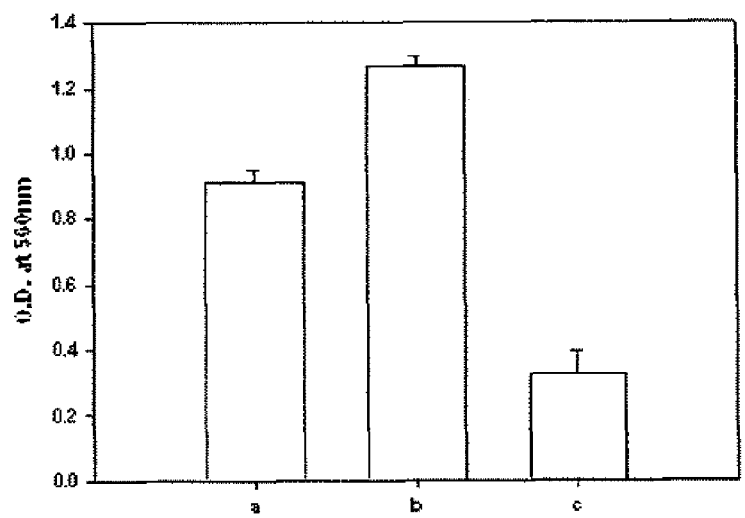

PREPARATION METHOD OF POROUS HYALURONIC ACID SPONGE FOR CELL DELIVERY SYSTEM

The present application claims priority to Korean Patent Application No. 10-2006-0040652 (filed on May 4, 2006), Korean Patent Application No. 10-2007-0042611 (filed May 2, 2007), and PCT Patent Application No. PCT/KR2007/002162 (filed May 2, 2007), all of which is hereby incorporated by reference in their entireties.

TECHNICAL FIELD

The present invention relates to preparation method of a porous hyaluronic acid sponge, more particularly to a preparation method of a porous hyaluronic acid sponge which supports cell growth inside the sponge, serves as scaffold for cell delivery and can be administrated through various administration routes.

BACKGROUND ART

Hyaluronic acid is a naturally occurring linear polysaccharide. It is a polymer of disaccharide units composed of β-1, 4-D-glucuronic acid and N-acetyl-D-glucosamine linked together by β-1,3-glycosidic bonds. Hyaluronic acid has a molecular weight ranging from 1,000 to 10,000,000 daltons.

Hyaluronic acid is the only non-sulfated glucosaminoglycan (GAG) found in the extracellular matrix (ECM) of higher animals.

Biomaterials derived from hyaluronic acid are used, for example, in regeneration of cartilage and skin. Also, they play key roles in drug delivery or surgery. Chemically unmodified hyaluronic acid is utilized as the aid for the delivery of ophthalmologic drug to improve the absorption of drugs and proteins at the mucosal tissue.

Further, with regard to the treatment of osteoarthritis, hyaluronic acid improves lubrication at the joint surface and thus reduces pain. Arthritis reduces the production of hyaluronic acid and the increased breakdown by proteases further reduces hyaluronic acid in the joint. As a result, the articular damage can be aggravated because external impact cannot be adequately absorbed or distributed at the joint.

Since approved by the FDA in 1997, the injection of hyaluronic acid is widely used. With compositions similar to those of the joint fluid, hyaluronic acid solution regains viscosity and elasticity when injected into the joint and improves lubrication and absorbs impact, thereby protecting the joint cartilage and preventing further damage.

Also, it is reported to have anti-inflammatory effect and inhibit the breakdown of chondrocytes by several in vitro researches. Based on this, it can be inferred that hyaluronic acid can be utilized as scaffold for cell delivery in the process of cell transplantation therapy of chondrocytes for cartilage tissue regeneration.

The in vivo metabolism of hyaluronic acid is regulated by hyaluronic acid synthase (HA synthase) and hyaluronidase. Hyaluronic acid synthase is an integral membrane enzyme, which synthesizes hyaluronic acid polymers and excretes them out of the cell. In mammals, HAS1, HAS2 and HAS3 isoenzymes are found.

Hyaluronidase is an enzyme that breaks down hyaluronic acid. Depending on the activation pH, it can be classified into neutral hyaluronidase and acidic hyaluronidase. Neutral hyaluronidase (PH-20) is specifically found in the testis (sperm) and shows activity in the physiological pH.

Acidic hyaluronidase (Hyal1-4) is found in body fluids as well as in a variety of human organs, including spleen, cartilage, skin, eyes, liver, kidney, bladder, placenta, etc., and shows activity around at pH 3. Since this enzyme is present in the lysosome, hyaluronic acid is transported into the cytoplasm by endocytosis and degraded.

The endocytosis of hyaluronic acid is mediated by the cell surface receptors. The primary cell surface receptor for HA is CD44. CD44 is a transmembrane glycoprotein and binds primarily to hyaluronic acid. It is expressed in most of human cell membranes. The hyaluronic acid fragments degraded at the lysosome induce different signal transfers depending on their size, affecting cell proliferation and differentiation.

Various porous scaffolds are used in the field of tissue engineering. Chondrocytes cultured in 2D condition such as petridish cannot maintain their chondrocytic phenotype, resulting in synthesis of type I collagen rather than type II.

In contrast, chondrocytes cultured in 3D condition maintain their characters and functions, resulting in spherical cell shape. That is, a 3-dimensional scaffold helps the cell attachment and cartilage formation in vitro and in vivo.

The use of porous scaffolds is very useful in that chondrocytes can be cultured under a restricted condition with significantly reduced necrosis of the tissue.

Thus, as one of new treatments for joint cartilage damage, the technique of culturing stem or progenitor cells derived from the cartilage, bone marrow or periosteum in vitro using biodegradable scaffolds and transplanting them into lesion site is attempted instead of direct injection of autologous chondrocytes.

This technique is advantageous over the method of using cell suspension since necrosis of the cartilage tissue to serve as cell sources is significantly reduced and the cells can be incubated under a restricted condition. Further, it is also adequate considering that cell attachement is improved by a scaffold.

In addition to cell delivery, a scaffold can serve as mold to fill lesion site of tissue. An ideal scaffold is required to be non-immunogenic, non-toxic, biocompatible, biodegradable and easy to manipulate.

The pore size of the scaffold is important. An inadequate pore size may result in the restricted nutrient supply to the cells being cultured in the scaffold or ineffective removal of the wastes from the cells.

If the pore size is too small, the cells may not be completely filled inside the scaffold, which negatively affects the generation of the tissue. In contrast, if the pore size is too large, not all the extracellular matrix proteins synthesized by cells are accumulated. That is, the proteoglycan and collagen accumulated in the scaffold can be found only a part of the total degree of actually synthesized ECM.

Accordingly, even though chondrocytes cultured in a porous scaffold in a metabolically active state, the scaffold may deem as inadequate for the growth of chondrocytes.

Thus, the control of the pore size is important in improving the retention rate of newly synthesized extracellular matrix molecules inside the scaffold.

Also, in case the sponge type scaffold with minimal porosity required for survival, growth and differentiation of cells is in solid state, it comes into problem that the surgical operation is the only way of delivering the entire scaffold including cells to a disease site.

DISCLOSURE OF INVENTION

Technical Problem

The present inventors completed the present invention by developing a porous hyaluronic acid sponge which enables stable cell cultivation, offers controllable microenvironment for cell culture through controlling the pore size of the sponge and allows cell delivery through various administration routes including injection.

Accordingly, an object of the present invention is to provide a preparation method of a porous hyaluronic acid sponge the pore size of which can be controlled to ensure cell growth.

Another object of the present invention is to provide a preparation method of a gel-state porous hyaluronic acid sponge comprising hyaluronic acid, an aqueous sodium hydroxide solution and an epoxy-based crosslinking agent with given compositions, which allows the delivery of the entire scaffold including cells to a disease site through various administration routes other than surgical operation.

Still another object of the present invention is to provide a porous hyaluronic acid sponge prepared by the aforementioned methods and a cell delivery system using the same.

Technical Solution

To attain the objects, the present invention provides a preparation method of a porous hyaluronic acid sponge comprising the steps of: dissolving hyaluronic acid in an aqueous sodium hydroxide solution; adding an epoxy-based crosslinking agent to the aqueous sodium hydroxide solution in which hyaluronic acid is dissolved and homogenizing the hyaluronic acid solution; hydrogelating the homogenized hyaluronic acid solution; washing the hydrogelated hyaluronic acid hydrogel with ultrapure water; swelling the washed hyaluronic acid hydrogel to obtain porosity; and freeze-drying the hyaluronic acid hydrogel to obtain a porous hyaluronic acid sponge.

Advantageous Effects

The preparation method of a porous hyaluronic acid sponge in accordance with the present invention offers a scaffold in which cells can be cultured stably, provides pores which are essential for the cell survival through swelling and allows the control of the microenvironment for cell culture through the control of the pore size of the porous hyaluronic acid sponge with the swelling time.

Particularly, since the sponge can be prepared not only into solid but also into gel, cell delivery to the disease site can be accomplished through various administration routes, not only by surgical operation but also by direct injection, application on skin, and so forth.

BRIEF DESCRIPTION OF THE DRAWINGS

FIG. 1 illustrates a flowchart for the preparation method of a porous hyaluronic acid sponge according to the present invention.

FIG. 2 shows the photograph of the porous hyaluronic acid sponge prepared by the preparation method of a porous hyaluronic acid sponge according to the present invention.

FIG. 3 is the scanning electron micrograph (SEM) of the porous hyaluronic acid sponge shown in FIG. 2.

FIG. 4 shows the photograph of the gellable porous hyaluronic acid sponges according to the present invention after 2 days of swelling (each of 1.25 g and 2.50 g of hyaluronic acid was added to each of upper and lower rows; the PEGDG contents were 1.0 mL, 2.5 mL and 5.0 mL from left to right).

FIG. 5 shows the photograph of taking cells and the gellable porous hyaluronic acid sponge of the present invention after culturing the cells for 4 weeks in the sponge with a syringe.

FIG. 6 shows the scanning electron micrograph of the porous hyaluronic acid sponge prepared in Example 1.

FIG. 7 shows the scanning electron micrograph of the porous hyaluronic acid sponge prepared in Example 2.

FIG. 8 shows the scanning electron micrograph of the porous hyaluronic acid sponge prepared in Example 3.

FIG. 9 shows the scanning electron micrograph of the porous hyaluronic acid sponge prepared in Example 4.

FIG. 10 shows the scanning electron micrograph of the porous hyaluronic acid sponge prepared in Example 5.

FIG. 11 shows the scanning electron micrograph of the chondrocytes cultured in the porous hyaluronic acid sponge prepared in Example 2.

FIG. 12 shows the optical micrograph of the chondrocytes cultured in the porous hyaluronic acid sponge prepared in Example 2 after the MTT staining.

FIG. 13 is a graph showing the change of the number of living chondrocytes cultured in the porous hyaluronic acid sponge prepared in Example 2 with time.

FIG. 14 shows the RT-PCR result for the aggrecan (a) and type II collagen (b) in the stem cells to be differentiated into chondrocytes in the porous hyaluronic acid sponge prepared in Example 2.

FIG. 15 shows the inside of the Alcian blue-stained porous hyaluronic acid sponge prepared in Example 2

FIG. 16 shows the graphs showing the change of the number of living chondrocytes cultured in the porous hyaluronic acid sponges prepared in Examples 6 to 8 with time.

FIG. 17 shows the RT-PCR result for the aggrecan (a) and type II collagen (b) in the stem cells to be differentiated into chondrocytes in the porous hyaluronic acid sponges prepared in Examples 6 to 8.

FIG. 18 is a graph showing the change of the number of living chondrocytes cultured in the porous hyaluronic acid sponge prepared in Example 9 with time.

FIG. 19 shows the scanning electron micrograph of the hyaluronic acid sponge prepared in Example 10.

FIG. 20 shows the graphs showing the change of the number of living chondrocytes after being cultured in the gellable porous hyaluronic acid sponges prepared in Examples 6(a) and 7(b) and the hyaluronic acid sponge prepared in Example 10(c) for 1 day.

BEST MODE FOR CARRYING OUT THE INVENTION

The present invention provides a preparation method of a porous hyaluronic acid sponge comprising the steps of: dissolving hyaluronic acid in an aqueous sodium hydroxide solution; adding an epoxy-based crosslinking agent to the aqueous sodium hydroxide solution in which hyaluronic acid is dissolved and homogenizing the hyaluronic acid solution; hydrogelating the homogenized hyaluronic acid solution; washing the hydrogelated hyaluronic acid hydrogel with ultrapure water; swelling the washed hyaluronic acid hydrogel to obtain porosity; and freeze-drying the hyaluronic acid hydrogel to obtain a porous hyaluronic acid sponge.

In the present invention hyaluronic acid having a number-average molecular weight ranging from 1,000,000 to 5,000,000 daltons (Da) is used. The concentration of the aqueous sodium hydroxide solution used in the dissolution step is preferably from 0.05 to 1.0 N, more preferably from 0.1 to 0.3 N.

And, the hydrogelation of the homogenized hyaluronic acid solution is preferably performed at 40 to 80° C. for 1 to 6 hours, more preferably at 55 to 65° C. for 1 to 3 hours.

And, the swelling of the hyaluronic acid hydrogel is preferably performed for 1 to 7 days using ultrapure water.

And, preferably, the epoxy-based crosslinking agent used in the homogenization step is selected from the group consisting of polyethylene glycol diglycidyl ether, epichlorohydrin, methyl glycidyl ether, phenyl glycidyl ether, lauryl alcohol glycidyl ether, ethylene glycol dimethacrylate, 1,4-butanediol diglycidyl ether and ethylene glycol diglycidyl ether.

The present invention also provides a porous hyaluronic acid sponge which is prepared by the aforesaid preparation method and has a pore size of 30 to 500 □.

The present invention further provides a cell delivery system using the aforesaid porous hyaluronic acid sponge as scaffold for delivering cells.

Preferably, the cells are selected from the group consisting of chondrocytes, stem cells, neurocytes, brain cells, myocytes, sensory cells and blood cells.

Hereinafter, the present invention is described in more detail referring to the attached drawings.

The preparation method of a porous hyaluronic acid sponge according to the present invention comprises a dissolution step (S101), a homogenization step (S102), a hydrogelation step (S103), a washing step (S104), a swelling step (S105) and a freeze-drying step (S106).

The dissolution step (S101) is the step of dissolving hyaluronic acid in a solvent to obtain a hyaluronic acid solution. The solvent may be an aqueous sodium hydroxide solution having a concentration of 0.05 N to 1.0 N, preferably an aqueous sodium hydroxide solution having a concentration of 0.1 N to 0.3 N.

The pore size of the porous hyaluronic acid sponge prepared according to the present invention can be controlled by changing the concentration of the sodium hydroxide solution.

If the concentration of the aqueous sodium hydroxide solution is below 0.05 N, the sponge becomes too soft, resulting in problems with regard to cell injection and cultivation. In contrast, if the concentration of the aqueous sodium hydroxide solution exceeds 1.0 N, the sponge becomes too stiff, resulting in a scaffold that cannot be seen as sponge.

The homogenization step (S102) is the step in which the dissolved hyaluronic acid solution is homogenized after adding a crosslinking agent. The homogenization is performed for 5 to 20 minutes using a mechanical stirrer at 800 to 1200 rpm.

If a porous hyaluronic acid sponge is prepared without adding a crosslinking agent, a porous hyaluronic acid sponge which is readily soluble in water is attained.

Such a porous hyaluronic acid sponge cannot serve as stable scaffold for cell cultivation. Accordingly, in the preparation method of a porous hyaluronic acid sponge according to the present invention, the step of adding a crosslinking agent is performed to improve the water insolubility of the porous hyaluronic acid sponge.

For the crosslinking agent, preferably a non-cytotoxic and economical epoxy compound, for example, selected from the group consisting of polyethylene glycol diglycidyl ether, epichlorohydrin, methyl glycidyl ether, phenyl glycidyl ether, lauryl alcohol glycidyl ether, ethylene glycol dimethacrylate, 1,4-butanediol diglycidyl ether and ethylene glycol diglycidyl ether is used.

The epoxy-based crosslinking agent is preferably used in 1 to 50 parts by weight per 100 parts by weight of the hyaluronic acid solution. If the epoxy-based crosslinking agent is used less than the aforesaid range, the sponge may become useless because of inadequate crosslinking.

In contrast, if more than 50 parts by weight of the epoxy-based crosslinking agent is used per 100 parts by weight of the hyaluronic acid solution, excess epoxy-based crosslinking agents remain. Since the excess epoxy-based crosslinking agents have to be removed in the washing step (S104), such a situation is not good in both economy and efficiency.

Particularly, a porous hyaluronic acid sponge that transforms into a gel phase after a given period of the cell cultivation is attained when 3 to 10 parts by weight of an epoxy-based crosslinking agent is used per 100 parts by weight of the hyaluronic acid solution.

The hydrogelation step (S103) is the step in which the solution homogenized in the homogenization step (S102) is hydrogelated by crosslinking. The hydrogelation step (S103) is performed preferably at 40 to 80° C. for 1 to 6 hours, more preferably at 55 to 65° C. for 1-3 hours.

If the temperature or time falls outside the aforesaid range, crosslinking does not occur at all or, even if it does, the resultant hyaluronic acid sponge is decomposed in short time. Such a hyaluronic acid sponge does not provide sufficient pores required for cell cultivation.

The washing step (S104) is the step in which the hydrogelated hyaluronic acid hydrogel is washed. In this step, unreacted residues of the hyaluronic acid hydrogel, for example, excess crosslinking agent and sodium hydroxide, are removed to provide an environment adequate for cell cultivation. Preferably, ultrapure water is used for the washing.

The swelling step (S105) is the step in which the washed hyaluronic acid hydrogel is swollen. Preferably, the swelling step (S105) is performed by swelling the hyaluronic acid hydrogel in ultrapure water for 1 to 7 days. However, the solution used in the washing step (S104) and the swelling step (S105) is not limited to ultrapure water. Various buffer solutions may be used, too.

When a hyaluronic acid sponge is prepared by swelling the hyaluronic acid hydrogel for less than 1 day, the pore size may change as the hyaluronic acid sponge swells further by the medium used for cell cultivation.

Particularly, if the swelling step is omitted, the pore size becomes so small that the cells cannot be held inside the scaffold. Further, the supply of nutrients to cells or the removal of wastes may be ineffective.

FIG. 19 shows the scanning electron micrograph of the hyaluronic acid sponge prepared without the swelling step and FIG. 20 shows the graphs showing the change of the number of living chondrocytes after being cultured in the gellable porous hyaluronic acid sponges [(a), (b)] and the porous hyaluronic acid sponges (c) prepared without the swelling step for 1 day.

Although dependent upon the kind of the sponge, the pore size of the sponge prepared by swelling the hyaluronic acid hydrogel for over 7 days is not significantly different from the pore size of the sponge prepared swelling for 7 days. Thus, a swelling period of over 7 days is not efficient in time and cost.

The freeze-drying step (S106) is the step in which the hyaluronic acid hydrogel is freeze-dried to obtain a porous hyaluronic acid sponge. The freeze drying is performed in a freezer of −20 to −152° C. for about 24 hours and then at −50 to −80° C. and 8 to 15 □Hg for at least 48 to 72 hours.

The resultant hyaluronic acid sponge is shown in FIG. 2. And, FIG. 3 shows the scanning electron micrograph of the hyaluronic acid sponge. Referring to the figures, the porous hyaluronic acid sponge (100) has a plurality of pores (101) inside.

Particularly, although the porous hyaluronic acid sponge according to the present invention is generally in solid state, a solid porous hyaluronic acid sponge prepared with 3 to 10 parts by weight of an epoxy-based crosslinking agent per 100 parts by weight of the hyaluronic acid solution obtained by dissolving hyaluronic acid in an aqueous sodium hydroxide solution may be transformed into a fluid, gel-state porous hyaluronic acid sponge by cultivation for a given time.

The phase transformation of the sponge can be attained by optimizing the proportion of the hyaluronic acid, the aqueous sodium hydroxide solution and the epoxy-based crosslinking agent. By culturing cells in the solid porous hyaluronic acid sponge for a given period of time, e.g., for 1 to 4 weeks, a required fluidity may be attained at the time of administration.

FIG. 4 shows the photograph of the porous hyaluronic acid sponge after 2 days of swelling. And, FIG. 5 shows the photograph of taking cells and the porous hyaluronic acid sponge after culturing the cells for 4 weeks with a 17 gauge syringe.

Referring to the figures, the gellable porous hyaluronic acid sponge according to the present invention is fluid and thus can be taken with a syringe. Consequently, it can be delivered to a disease site using a cell-scaffold structure without surgical operation or directly applied to skin or mucosa. As a result, the porous hyaluronic acid sponge can be utilized widely.

The porous hyaluronic acid sponge (100) of the present invention has a pores (101) ranging from 30 to 500☐. Thus, using the porous hyaluronic acid sponge (100), chondrocytes, stem cells, neurocytes, brain cells, myocytes, sensory cells or blood cells may be proliferated, differentiated and injected to the disease site for treatment.

For example, chondrocytes may be proliferated and differentiated using the porous hyaluronic acid sponge of the present invention as scaffold and then injected to a damaged cartilage to treat arthritis.

A preferable pore size of the pores (101) is dependent on the cells, but 30 to 500☐ is preferable. If the pore size of the pores (101) is smaller than 30☐, there may be a problem in supplying nutrients to the cells or removing wastes.

And, if the pore size of the pores (101) is larger than 500☐, the cells are not properly attached to the hyaluronic acid sponge (100) and the cells may not be differentiated properly even if the cells cultured in the sponge are in metabolically activated state.

For example, when chondrocytes are cultured in a hyaluronic acid sponge having a large pore size, the retention rate of collagen or proteoglycan of the chondrocytes decreases, resulting in an inadequate environment for cell cultivation.

MODE FOR THE INVENTION

EXAMPLES

Practical and preferred embodiments of the present invention are illustrated as shown in the following examples. However, it will be appreciated that those skilled in the art may, in consideration of this disclosure, make modifications and improvements within the spirit and scope of the present invention.

Example 1 and Example 2

The change of the pore size of the porous hyaluronic acid sponge of the present invention depending on the concentration of the aqueous sodium hydroxide solution is investigated by giving Example 1 and Example 2.

1.0 g of hyaluronic acid having a molecular weight of 1,500,000 daltons (Da) was dissolved in a 0.1 N aqueous sodium hydroxide solution (Example 1) and the same hyaluronic acid was dissolved in a 0.3 N aqueous sodium hydroxide solution (Example 2).

2 mL of PEGDG (polyethylene glycol diglycidyl ether) was added to each 5.6 mL of the solutions prepared in Example 1 and Example 2 as crosslinking agent.

The crosslinked solutions were hydrogelated at 60° C. for 3 hours. The resultant hyaluronic acid hydrogels were washed with ultrapure water to remove unreacted residuals present in the hyaluronic acid hydrogels.

Then, the hydrogels were swollen with ultrapure water for 7 days. The swollen hyaluronic acid hydrogels were frozen in a −80° C. freezer for 24 hours and then freeze-dried at −50° C. and 100 ☐Hg for 48 hours to obtain hyaluronic acid sponges.

The porous hyaluronic acid sponge prepared in Example 1 is shown in FIG. 6 and the porous hyaluronic acid sponge prepared in Example 2 is shown in FIG. 7.

Referring to the figures, pores (201) are formed inside the porous hyaluronic acid sponge (200) prepared in Example 1. Also, pores (301) are formed inside the porous hyaluronic acid sponge (300) prepared in Example 2.

Comparing the pores (201) formed inside the porous hyaluronic acid sponge (200) prepared in Example 1 and the pores (301) formed inside the porous hyaluronic acid sponge (300) prepared in Example 2, it can be seen that the pores (201) formed inside the porous hyaluronic acid sponge (200) prepared in Example 1 are larger.

Thus, it can be seen that the swelling step proceeds faster as the concentration of sodium hydroxide decreases and, as a result, a porous hyaluronic acid sponge having a larger pore size is obtained. To the contrary, the swelling step proceeds more slowly as the concentration of sodium hydroxide increases and the strength of the porous hyaluronic acid sponge obtained after the freeze drying increases. Consequently, the resultant porous hyaluronic acid sponge may be easily shaped into a structure adequate for cell growth.

From these results, it can be seen that the microenvironment for cell culture can be adjusted by controlling the pore size of the porous hyaluronic acid sponge.

Example 3 to Example 5

The change of the pore size of the porous hyaluronic acid sponge of the present invention depending on the concentration of the swelling time during the swelling step is investigated.

1.0 g of hyaluronic acid having a molecular weight of 1,500,000 daltons (Da) was dissolved in a 0.1 N aqueous sodium hydroxide solution and 2.0 mL of PEGDG (polyethylene glycol diglycidyl ether) was added to 5.6 mL of the resultant solution as crosslinking agent.

The crosslinked solution was hydrogelated at 60° C. for 3 hours. The resultant hyaluronic acid hydrogel was washed with ultrapure water to remove unreacted residuals present in the hyaluronic acid hydrogel.

Then, the hyaluronic acid hydrogel was swollen using a PBS (phosphate buffered saline) solution for 1 day (Example 3), for 4 days (Example 4) and for 7 days (Example 5).

The hyaluronic acid hydrogels prepared in Example 3, Example 4 and Example 5 were frozen in a −80° C. freezer for 24 hours and then freeze-dried at −50° C. and 10 ☐Hg for 48 hours to obtain hyaluronic acid sponges.

The scanning electron micrographs of the porous hyaluronic acid sponges prepared in Example 3, Example 4 and Example 5 are shown in FIGS. 8 to 10, respectively.

Referring to the figures, pores (410) are formed inside the porous hyaluronic acid sponge (400) prepared in Example 3.

Pores (510) are also formed inside the porous hyaluronic acid sponge (500) prepared in Example 4. Pores (610) are formed inside the porous hyaluronic acid sponge (600) prepared in Example 5, too.

From the figures, it can be seen that the pore size of the porous hyaluronic acid sponge becomes different depending on the swelling time in the PBS solution.

To explain in detail, a longer swelling time results in a weaker strength of the hydrogel and more pore generation. As a result, a sponge with larger pore size is obtained following the freeze drying.

In Example 3, Example 4 and Example 5, PBS solution was used in the swelling step. The use of the PBS solution resulted in less swelling and increased strength of the porous hyaluronic acid sponge obtained following the freeze drying than when ultrapure water was used.

Testing Example 1

It was investigated if chondrocytes survive and proliferate in the pores of the porous hyaluronic acid sponge prepared in Example 2 and if adipose-derived stem cells (ADSCs) obtained from the human fat tissue are differentiated into chondrocytes.

1) Viability of Cells $1 \times 10^6$ chondrocytes were cultured in the porous hyaluronic acid sponge prepared in Example 2. Samples were taken and fixed in the Karnovsky's fixative at 4° C. for 2 hours.

The chondrocytes were cell lines obtained from the chondrocytes of the human rib and had been distributed from the Biochemical Lab of Kyungpook National University. The Karnovsky's fixative was prepared by dissolving 2 wt % of glutaraldehyde, 2 wt % of paraformaldehyde and 0.5 wt % of calcium chloride ($CaCl_2$) in a 0.05 M cacodylate buffer (pH 7.4).

After washing 3 times with a cacodylate buffer for 10 minutes, the sample was fixed in a 1% osmium tetroxide fixative. Subsequently, the sample was immersed in an ethanol solution to remove the moisture contained in the sample. The ethanol concentration of the ethanol solution was increased gradually, so that the dehydration occurred gradually.

Physical drying followed the dehydration with ethanol. The physical drying was performed using isoamyl acetate. The sample was completely dried using a critical point dryer. The sample was attached to a metal stub. After coating with gold, the sample was observed by scanning electron microscopy.

FIG. 11 shows the scanning electron micrograph (SEM) of the chondrocytes cultured in the porous hyaluronic acid sponge prepared in Example 2. It can be seen that there are numbers of chondrocytes (302) in the pores of the porous hyaluronic acid sponge (300).

The following test was preformed using an MTT solution in order to check the viability of the chondrocytes present in the porous hyaluronic acid sponge.

MTT stains living cells with deep purple color. An MTT (3.4.5-dimethylthiazol-3,5-diphenyltetrazolium bromide) solution was added to the sample. The sample was observed with an optical microscope after rendering the sample at 37° C. and 5% $CO_2$ for 3 hours. FIG. 12 shows the optical micrograph of the chondrocytes cultured in the porous hyaluronic acid sponge seen in FIG. 7. Referring to FIG. 12, it can be seen that there are numbers of living chondrocytes (302) inside the pores of the porous hyaluronic acid sponge (300).

2) Proliferation of Cells

The number of living cells was measured at different cultivation period in order to confirm if the cells proliferate well in the porous hyaluronic acid sponge.

After culturing chondrocytes in the porous hyaluronic acid sponge for 1 day, 4 days, 7 days and 14 days, an MTT solution (0.5 mg/mL) was added to the sample. Then, the sample was kept at 37° C. and 5% $CO_2$ for 4 hours to stain the living cells.

Subsequently, the culture medium was removed absorbance was measured at 560 nm after adding DMSO (dimethyl sulfoxide). The result is shown in FIG. 13.

FIG. 13 is a graph showing the change of the number of living chondrocytes cultured in the porous hyaluronic acid sponge prepared in Example 2. The abscissa is the incubation time and the ordinate is the absorbance of samples at 560 nm.

Referring to FIG. 13, it can be seen that the absorbance increases with incubation time. Thus, it can be seen that the chondrocytes proliferate well inside the hyaluronic acid sponge.

3) Differentiation of Cells

Using RT-PCR, it was investigated if the stem cells (ADSCs) obtained from the human fat tissue (processed lipoaspirate, PLA) are differentiated into chondrocytes inside the pores of the porous hyaluronic acid sponge.

The stem cells were undifferentiated cell lines obtained from the human fat tissue through liposuction and had been distributed from the Prostemics. The samples for the differentiation test were prepared by seeding the stem cells inside the porous hyaluronic acid sponge, culturing in a cell incubator at 5% $CO_2$ and 37° C. for 7 days, 10 days and 14 days using a DMEM medium containing 1% serum, TGF-β1 (10 ng/mL), ascorbate (50 nM), ITS (5□/mL) and dexamethasone (100 nM), transferring the cell-sponge system into a 1.5 mL Eppendorf tube, washing off the excess medium with PBS and cooling at −80° C.

A lysis buffer was added to the samples to extract RNAs from the cells. A reaction solution containing PCR buffer, dNTP mixture, RNase inhibitor and oligo dT primer was prepared. After adding the RNAs to the reaction solution, reverse transcription of synthesizing DNA from RNA was performed for 30 minutes at 60° C., for 5 minutes at 99° C. and for 5 minutes at 5° C.

To the resultant reverse transcription reaction solution, PCR buffer, Taq polymerase and each primer was added. Reaction was performed at 10 minutes at 95° C. Then, the cycle of 1 minute at 95° C., 1 minute at 60° C. and 1 minute at 72° C. was repeated for 31 times. Subsequently, reaction was further performed for 10 minutes at 72° C.

Whether the stem cells (ADSCs) derived from the human fat cells were differentiated into chondrocytes inside the hyaluronic acid sponge can be confirmed by the presence of type II collagen gene or aggrecan gene.

RT-PCR was performed using the pair of the nucleotide sequences of SEQ ID NO: 1 and SEQ ID NO: 2 as a primer in order to utilize the aggrecan gene as chondrogenic differentiation marker and using the pair of the nucleotide sequences of SEQ ID NO: 3 and SEQ ID NO: 4 as another primer in order to utilize the type II collagen gene as differentiation marker. The RT-PCR result is shown in FIG. 14.

FIG. 14 shows the RT-PCR result for the stem cells to be differentiated into chondrocytes in the porous hyaluronic acid sponge prepared in Example 2.

Referring to FIG. 14, two amplified bands were observed. One was that of aggrecan [(a), 501 bp] and the other band was that of type II collagen [(b), 379 bp].

Thus, it is clear that the stem cells were differentiated into chondrocytes in the porous hyaluronic acid sponge. Also, it can be seen that the chondrogenic differentiation of stem cells occurs actively and constantly since the bands for the aggrecan and type II collagen are thickened with cultivation time.

In FIG. 14, lane 1 is for 100 bp marker and lane 2 is the RT-PCR result for the RNAs extracted from the stem cells that have been cultured for 7 days. Lanes 3 and 4 in FIG. 14 are the RT-PCR for the RNAs extracted from the stem cells that have been cultured for 10 days and 14 days, respectively.

The marker for chondrogenic differentiation was stained with Alcian blue to investigate if the chondrocytes maintain their characteristics inside the pores of the porous hyaluronic acid sponge. Alcian blue selectively stains s-GAG (sulfate-glucosaminoglycan), the marker for chondrogenic differentiation.

Chondrocytes were cultured inside the pores of the porous hyaluronic acid sponge and were fixed using 4% paraformaldehyde at room temperature for 15 minutes. Subsequently, the sample was washed with a PBS solution and stained with Alcian blue at room temperature for 30 minutes.

The Alcian blue dye was prepared by dissolving Alcian blue in 0.1 N hydrochloric acid (HCl) to 1%. After staining, the sample was washed with 0.1 N hydrochloric acid for 5 minutes and observed with an optical microscope.

The optical micrograph is shown in FIG. 15. FIG. 15 shows the inside of the Alcian blue-stained porous hyaluronic acid sponge prepared in Example 2.

Referring to FIG. 15, it can be confirmed that the s-GAG, the marker for chondrogenic differentiation, present inside the pores of the porous hyaluronic acid sponge (300) is stained with Alcian blue (303).

Accordingly, it can be seen that the stem cells are differentiated into chondrocytes inside the pores of the porous hyaluronic acid sponge and maintain their characteristics. To conclude, it can be seen that the pores of the porous hyaluronic acid sponge provide the environment in which the cells are differentiated into chondrocytes and maintain chondrocytic characteristics.

Example 6

The process in which the porous hyaluronic acid sponge turns from the solid phase to the gel phase is investigated after culturing cells inside the porous hyaluronic acid sponge for a given period of time.

To 14 mL of a solution in which 1.25 g of hyaluronic acid having a molecular weight of 1,500,000 daltons (Da) was dissolved in a 0.1 N aqueous sodium hydroxide solution was added 1 mL of PEGDG (polyethylene glycol diglycidyl ether) as crosslinking agent. Following the crosslinking, the resultant hydrogel was prepared into a gellable hyaluronic acid sponge in the same manner as in Example 1, except that the swelling was performed for 2 days using ultrapure water.

FIG. 5 shows the photograph of taking cells and the gellable porous hyaluronic acid sponge of prepared in Example 6 after culturing chondrocytes for 4 weeks in the sponge with a syringe. It was confirmed that the gellable porous hyaluronic acid sponge turns into fluid gel state when the cells are cultured for a given period of time.

Example 7 and Example 8

The degree of swelling of the hyaluronic acid sponge depending on the addition amount of the PEGDG crosslinking agent is investigated.

Gellable porous hyaluronic acid sponges were prepared in the same manner as in Example 6, except that the addition amount of the PEGDG crosslinking agent was changed to 2.5 mL and 5.0 mL.

The upper row in FIG. 4 shows the degree of swelling of the gellable porous hyaluronic acid sponges prepared in Examples 6 to 8. It can be seen that the degree of swelling decreases as the addition amount of the crosslinking agent increases.

And, the bottom row in FIG. 4 shows the degree of swelling of the gellable porous hyaluronic acid sponges prepared by adding each 1.0 mL, 2.5 mL and 5.0 mL of the PEGDG crosslinking agent to 14 mL of a solution in which 2.50 g of hyaluronic acid is dissolved in a 0.3 N aqueous sodium hydroxide solution. As in the gellable porous hyaluronic acid sponges, it can be seen that the degree of swelling decreases as the addition amount of the crosslinking agent increases.

Testing Example 2

It was investigated if chondrocytes survive in the gellable hyaluronic acid sponges prepared in Examples 6 to 8 and if the stem cells (ADSCs) obtained from the human fat tissue are differentiated into chondrocytes.

1) Proliferation of Cells $1 \times 10^6$ chondrocytes were grown in the gellable porous hyaluronic acid sponges prepared in Examples 6 to 8 for 3 weeks and samples were taken. The chondrocytes were cell lines obtained from the joints of New Zeeland white rabbits.

The following test was preformed using an MTT solution in order to check the proliferation of chondrocytes present in the gellable porous hyaluronic acid sponges.

After 1 week, 2 weeks and 3 weeks of growing the chondrocytes in the gellable porous hyaluronic acid sponges prepared in Examples 6 to 8, the MTT solution (0.5 mg/mL) was added to each sample. Then, the samples were kept at 37° C. and 5% $CO_2$ for 4 hours to stain the living chondrocytes.

Subsequently, the medium was removed from the samples and DMSO (dimethyl sulfoxide) was added. Measurement of absorbance at 560 nm showed that the number of living cells was maintained without significant difference (FIG. 16).

2) Differentiation of Cells

Differentiation of cells was investigated in the same manner as in Testing Example 1, except for using the gellable porous hyaluronic acid sponges prepared in Examples 6 to 8.

As seen in FIG. 17, two amplified bands were observed. One was that of aggrecan [(a), 501 bp] and the other band was that of type II collagen [(b), 379 bp].

Thus, it is clear that the stem cells were differentiated into chondrocytes in the gellable porous hyaluronic acid sponge. Also, it can be seen that the chondrogenic differentiation of stem cells occurs actively and constantly since the bands for the aggrecan and type II collagen were thickened with cultivation time.

In FIG. 17, lane 1 is for 100 bp marker and lanes 2 and 3 are the RT-PCR results for the RNAs extracted from the stem cells that have been cultured for 7 days and 14 days, respectively.

Example 9

The change of the number of living cells depending on the swelling time is investigated.

Gellable hyaluronic acid sponges were prepared as in Examples 6 to 8, except for performing the swelling for 4 days using ultrapure water.

After culturing chondrocytes in the gellable hyaluronic acid sponges for 0 week, 1 week and 2 weeks, the number of living cells was counted in the same manner as in Testing Example 2. The result is shown in FIG. 18.

Referring to FIG. 18, it can be seen that the number of living cells decrease with incubation time. Thus, it can be seen that the increase of the swelling time from 2 days to 4 days had negative effect on the proliferation and viability of the cells.

Example 10

The change of the number of living cells depending on the pore size and the cultivation time in the hyaluronic acid sponge is investigated when the hyaluronic acid sponge is prepared without swelling.

A hyaluronic acid sponge was prepared in the same manner as in Example 6, except for omitting the swelling step.

FIG. 19 shows the scanning electron micrograph of the hyaluronic acid sponge prepared in Example 10. As seen in the figure, pores were hardly formed or, even if they were, the pore size of them was significantly smaller than that of pores seen in FIG. 3, FIG. 6, FIG. 7, FIG. 8, FIG. 9 and FIG. 10.

FIG. 20 shows the graphs showing the change of the number of living chondrocytes after being cultured in the gellable porous hyaluronic acid sponges prepared in Examples 6(a) and 7(b) and the hyaluronic acid sponge prepared in Example 10(c) for 1 day. The number of living chondrocytes was counted in the same manner as in Testing Example 2.

As seen in FIG. 20, when the cells were cultured in the hyaluronic acid sponge prepared without the swelling step (c), the number of living cells reduced significantly than when the cells were cultured in the gellable hyaluronic acid sponges [(a), (b)]. Consequently, it can be seen that the swelling step significantly affects the formation of pores, which are essential in the survival of cells, and the pore size.

While the present invention has been described in detail with reference to the preferred embodiments, those skilled in the art will appreciate that various modifications and substitutions can be made thereto without departing from the spirit and scope of the present invention as set forth in the appended claims.

INDUSTRIAL APPLICABILITY

The porous hyaluronic acid sponge prepared in accordance with the present invention serves as the scaffold in which cells can be cultured stably. Since the pore size of the porous hyaluronic acid sponge can be controlled, the microenvironment for cell culture can be adjusted. Particularly, cells can be cultured and delivered to the wanted disease site through various administration routes since the porous hyaluronic acid sponge can be prepared into not only solid but also fluid gel form.

The invention claimed is:

1. A preparation method of a porous hyaluronic acid sponge comprising the steps of:
    dissolving hyaluronic acid in an aqueous sodium hydroxide solution;
    adding an epoxy-based crosslinking agent to the aqueous sodium hydroxide solution in which hyaluronic acid is dissolved and homogenizing the hyaluronic acid solution;
    hydrogelating the homogenized hyaluronic acid solution;
    washing the hydrogelated hyaluronic acid hydrogel with ultrapure water to remove at least excess crosslinking agent;
    swelling the washed hyaluronic acid hydrogel solely with ultrapure water for 1 to 7 days to attain porosity; and
    freeze-drying the hyaluronic acid hydrogel to obtain a porous hyaluronic acid sponge,
    the sponge including a pore size of 30 μm to 500 μm as a scaffold for delivering cells, the cells selected from the group consisting of chondrocytes, stem cells, neurocytes, brain cells, myocytes, sensory cells and blood cells.

2. The preparation method of a porous hyaluronic acid sponge of claim 1, wherein the aqueous sodium hydroxide solution used in the dissolution step has a concentration of 0.05 N to 1.0 N.

3. The preparation method of a porous hyaluronic acid sponge of claim 1, wherein the hydrogelation step is performed by reacting the homogenized hyaluronic acid solution at 40 to 80° C. for 1 to 6 hours.

4. The preparation method of a porous hyaluronic acid sponge of claim 1, wherein the epoxy-based crosslinking agent used in the homogenization step is selected from the group consisting of polyethylene glycol diglycidyl ether, methyl glycidyl ether, phenyl glycidyl ether, lauryl alcohol glycidyl ether, 1,4-butanediol diglycidyl ether and ethylene glycol diglycidyl ether.

5. The preparation method of a porous hyaluronic acid sponge of claim 1, wherein the amount of crosslinking agent added to the porous hyaluronic acid sponge comprises 1 to 50 parts by weight of the epoxy-based crosslinking agent per 100 parts by weight of the hyaluronic acid solution in which hyaluronic acid is dissolved in the aqueous sodium hydroxide solution.

6. The preparation method of a porous hyaluronic acid sponge of claim 5, wherein the amount of crosslinking agent added to the porous hyaluronic acid sponge comprises 3 to 10 parts by weight of the epoxy-based crosslinking agent per 100 parts by weight of the hyaluronic acid solution in which hyaluronic acid is dissolved in the aqueous sodium hydroxide solution so that the sponge turns into a fluid gel phase when cells are grown for 1 to 4 weeks.

7. The preparation method of a porous hyaluronic acid sponge of claim 6, wherein the sponge turned into the fluid gel phase is injectably deliverable.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: RT-PCR primer for Human Aggrecan gene

<400> SEQUENCE: 1
aaaccacctc tgcattccac                                              20

<210> SEQ ID NO 2
<211> LENGTH: 20
<212> TYPE: DNA
<213> ORGANISM: Artificial Sequence
<220> FEATURE:
<223> OTHER INFORMATION: RT-PCR primer for Human Aggrecan gene

<400> SEQUENCE: 2
cctctgtctc cttgcaggtc                                              20

<210> SEQ ID NO 3
<211> LENGTH: 20
<212> TYPE: DNA
<213> ORGANISM: Artificial Sequence
<220> FEATURE:
<223> OTHER INFORMATION: RT-PCR primer for Collagen type II gene

<400> SEQUENCE: 3
ccgaggcaac gatggtcagc                                              20

<210> SEQ ID NO 4
<211> LENGTH: 21
<212> TYPE: DNA
<213> ORGANISM: Artificial Sequence
<220> FEATURE:
<223> OTHER INFORMATION: RT-PCR primer for Collagen type II gene
```

```
<400> SEQUENCE: 4 tgggccttg ttcacctttg a                                              21
```